US011272142B2

(12) United States Patent
Bresch et al.

(10) Patent No.: US 11,272,142 B2
(45) Date of Patent: Mar. 8, 2022

(54) SYSTEM AND METHOD FOR DETERMINING VITAL SIGN INFORMATION

(71) Applicant: KONINKLIJKE PHILIPS N. V., Eindhoven (NL)

(72) Inventors: Erik Bresch, Eindhoven (NL); Jens Muehlsteff, Aachen (DE); Rolf Neumann, Calw (DE); Mukul Julius Rocque, Eindhoven (NL); Willem Verkruijsse, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1376 days.

(21) Appl. No.: 14/192,905

(22) Filed: Feb. 28, 2014

(65) Prior Publication Data

US 2014/0253709 A1 Sep. 11, 2014

Related U.S. Application Data

(60) Provisional application No. 61/781,112, filed on Mar. 14, 2013, provisional application No. 61/773,438, filed on Mar. 6, 2013.

(30) Foreign Application Priority Data

Mar. 6, 2013 (EP) .................................. 13157992
Mar. 14, 2013 (EP) .................................. 13159110

(51) Int. Cl.
*H04N 7/18* (2006.01)
*A61B 5/00* (2006.01)
(Continued)

(52) U.S. Cl.
CPC ............. *H04N 7/18* (2013.01); *A61B 5/0037* (2013.01); *A61B 5/0077* (2013.01); *A61B 5/02416* (2013.01); *A61B 5/1127* (2013.01)

(58) Field of Classification Search
CPC ...... A61B 2090/3612; A61B 2090/371; A61B 5/0077; G06K 9/00221
(Continued)

(56) References Cited

U.S. PATENT DOCUMENTS 7,715,897 B2 5/2010 Coulston
8,634,591 B2 1/2014 Vincent
(Continued)

FOREIGN PATENT DOCUMENTS

DE 10335037 A1 3/2005
EP 2319406 5/2011
(Continued)

OTHER PUBLICATIONS

Verkruysse, W., et al.; Remote plethysmographic imaging using ambient light; 2008; Opt. Express; 16(26) 21434-21445.
(Continued)

*Primary Examiner* — Clifford Hilaire
*Assistant Examiner* — Kristin Dobbs

(57) ABSTRACT

In a system and method for determining vital sign information of a subject the subject is illuminated with radiation, and radiation reflected from the subject is received. A region of interest is located in a first phase. Said illumination is controlled to locally illuminate, in a second phase, the located region of interest with radiation allowing determination of vital sign information. Finally, vital sign information of the subject is determined from the radiation reflected from said region of interest and detected in said second phase.

20 Claims, 8 Drawing Sheets

(51) Int. Cl.
*A61B 5/024* (2006.01)
*A61B 5/11* (2006.01)

(58) Field of Classification Search
USPC .......................................................... 348/77
See application file for complete search history.

(56) References Cited

U.S. PATENT DOCUMENTS

| | | | |
|---|---|---|---|
| 9,218,668 | B2 | 12/2015 | Rocque |
| 9,615,749 | B2 | 4/2017 | Clifton |
| 2005/0228244 | A1 | 10/2005 | Banet |
| 2005/0277837 | A1 | 12/2005 | Coulston et al. |
| 2007/0183041 | A1 | 8/2007 | McCloy et al. |
| 2009/0051544 | A1 | 2/2009 | Niknejad |
| 2009/0187112 | A1 | 7/2009 | Meir et al. |
| 2009/0196475 | A1 | 8/2009 | Demirli et al. |
| 2009/0226071 | A1* | 9/2009 | Schuler ............. A61B 5/02416 382/133 |
| 2012/0022348 | A1 | 1/2012 | Droitcour et al. |
| 2012/0190944 | A1 | 7/2012 | Thaveeprungsriporn |
| 2013/0006093 | A1 | 1/2013 | Raleigh et al. |
| 2013/0035599 | A1 | 2/2013 | De Bruijn et al. |
| 2013/0053929 | A1* | 2/2013 | Colbaugh ............ A61M 21/02 607/90 |
| 2013/0226007 | A1* | 8/2013 | Jeanne ................ A61B 6/5288 600/473 |
| 2013/0294505 | A1 | 11/2013 | Kirenko |
| 2013/0296716 | A1* | 11/2013 | Kurzenberger .... G06K 7/10366 600/479 |

FOREIGN PATENT DOCUMENTS

| | | |
|---|---|---|
| EP | 2380493 A1 | 10/2011 |
| EP | 2438849 | 4/2012 |
| WO | 2011042851 | 4/2011 |
| WO | 2011063266 A2 | 5/2011 |
| WO | 2012013304 A1 | 2/2012 |
| WO | 2012093311 A1 | 7/2012 |

OTHER PUBLICATIONS

Caffier, et al., "Experimental evaluation of eye-blink parameters as a drowsiness measure"; European Journal of Applied Physiology; May 2003, vol. 89, Issue 3-4, pp. 319-325.

* cited by examiner

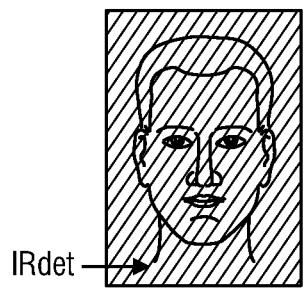 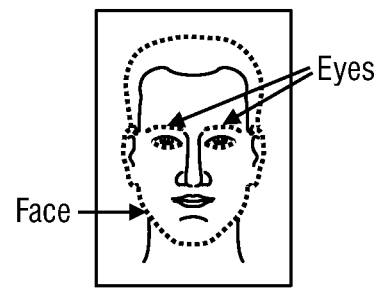 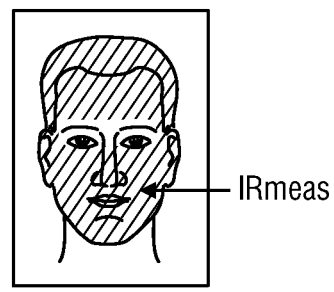
FIG.9A  FIG.9B  FIG.9C
 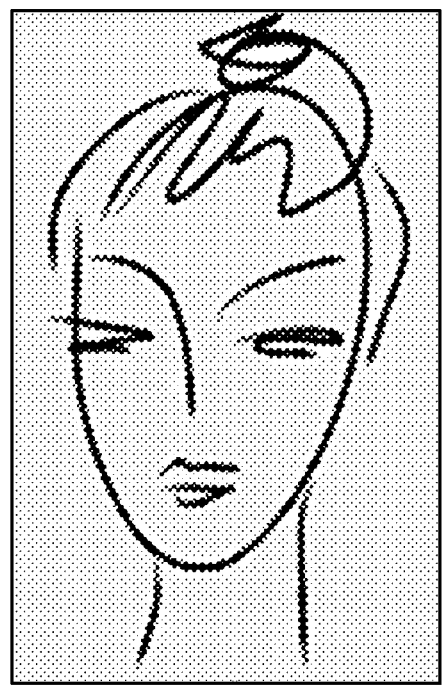
FIG.10A  FIG.10B

SYSTEM AND METHOD FOR DETERMINING VITAL SIGN INFORMATION

CROSS REFERENCE TO RELATED APPLICATIONS

This application claims the benefit of U.S. provisional application Ser. No. 61/773,438 filed Mar. 6, 2013 and European provisional application serial no. 13157992.2 filed Mar. 6, 2013 and U.S. provisional application Ser. No. 61/781,112 filed Mar. 14, 2013 and European provisional application serial no. 13159110.9 filed Mar. 14, 2013, all of which are incorporated herein by reference.

FIELD OF THE INVENTION

The present invention relates to a system method and computer program for determining vital sign information of a subject, in particular respiratory rate, pulse rate and/or oxygen saturation of a person.

BACKGROUND OF THE INVENTION

Unobtrusive vital sign monitoring using a video camera, or remote PPG (photoplethysmography), has been demonstrated and found relevant for patient monitoring. Remote photoplethysmographic imaging is, for instance, described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a selected region (typically part of the cheek in this system). By looking at periodic variations of this average signal, the heart beat rate and respiratory rate can be extracted. There are meanwhile a number of further publications and patent applications that describe details of devices and methods for obtaining vital signs of a patient by use of remote PPG.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal is a heartbeat signal in itself The normalized amplitude of this signal is different for different wavelengths, and for some wavelengths it is also a function of blood oxygenation or other substances found in blood or tissue.

Although regular video data have been shown to yield adequate vital signs (sometimes also called biometrical signals, such as heartbeat or pulse rate, respiration rate, oxygen saturation, etc.) in many cases, the image acquisition for challenging cases, like strong motion, low light levels, non-white illumination, needs further improvement. The known methods and devices are generally robust to motion and different lighting environments as long as one dominant light source is present. In such condition the PPG technology has proven to be accurate and robust up to a point that it can be used on a treadmill during fitness exercises One major problem encountered in image-based (e.g. camera-based) vital signs monitoring occurs when no dominant light is present in the environment. Further, a particular illumination is not always optimal for all measurements, e.g. for different skin types, body postures or after body movements.

Another challenging scenario is measuring vital sign information in darkness or in a low-light condition. For instance, for near-continuous monitoring of the vital signal information, e.g. oxygen saturation, of a patient in an intensive care unit (ICU) appropriate illumination (e.g. preferably in the visible spectrum, preferably in the green and/or red spectrum) has to be turned on every time a measurement is made in the room. This, however, can disrupt the patient's or other patients' sleep at night.

SUMMARY OF THE INVENTION

It is an object of the present invention to provide a system and method for accurate and reliable vital sign measurements even in darkness or low-light conditions while minimizing any disturbance to the subject, in particular a person or animal, and other persons nearby.

In a first aspect of the present invention, a system for determining vital sign information of a subject is presented comprising
an illumination device that illuminates the subject with radiation,
a detection device that receives radiation reflected from the subject,
a processing unit that locates a region of interest in a first phase,
a control unit that controls said illumination device to locally illuminate, in a second phase, the located region of interest with radiation allowing determination of vital sign information, and
an analysis unit that determines vital sign information of the subject from the radiation reflected from said region of interest detected in said second phase.

In a further aspect of the present invention a method for determining vital sign information of a subject is presented comprising
illuminating the subject with radiation,
receiving radiation reflected from the subject,
locating a region of interest in a first phase, to locally illuminate, in a second phase, the located region of interest with radiation allowing determination of vital sign information, and
determining vital sign information of the subject from the radiation reflected from said region of interest detected in said second phase.

In yet another aspect of the present invention, there is provided a computer program which comprises program code means for causing a computer to perform the steps of locating, controlling and determining of the proposed method when said computer program as carried out on a computer. Further, a non-transitory computer-readable recording medium that stores therein such a computer program product, which, when executed by a processor, causes said steps of the method disclosed herein to be performed, is presented.

Preferred embodiments of the invention are defined in the dependent claims. It shall be understood that the claimed method computer program and medium have similar and/or identical preferred embodiments as the claimed system and as defined in the dependent claims.

The present invention is based on the idea to guide a targeted (i.e. local) illumination of only the region of interest, in particular a skin patch (e.g. at the arm, hand, neck, face or chest) from which the optical measurement is produced. This provides that the light pollution in the room is minimized and that the person (e.g. a patient) himself as well as other persons nearby remain undisturbed by the visible illumination so that they can, for instance, sleep with as little disturbance as possible.

In a first step the region of interest is located. The location can be done with known image processing techniques by using anatomic properties of the subject. A first example would be to identify the patient's contour and/or the contour of the different body parts (head, arms, legs, chest, abdomen or back) e.g. in contrast to the mattress or by searching for skin color areas. A face recognition algorithm can support this process by identify the face and allowing to identify the patients position (lying face up vs. face down).

In one embodiment the identified face is intentionally excluded as region of interest to avoid disturbance to the patient. In another embodiment the identified eyes and the mouth are used to locate the forehead as a region of interest relative to the eyes and mouth. In another embodiment a marker is used to locate the region of interest or to support locating the region of interest.

Once the region of interest is located this information is used to guide a targeted illumination of only the region of interest, in particular a skin patch (e.g. at the arm, hand, neck, face or chest) from which the optical measurement is produced. This provides that the light pollution in the room is minimized and that the person (e.g. a patient) himself as well as other persons nearby remain undisturbed by the visible illumination so that they can, for instance, sleep with as little disturbance as possible.

In many cases the location of the region of interest in the first phase is possible by using the available illumination in the room, i.e. in the first phase no additional illumination is provided. In a preferred embodiment, however, an illumination in the non-visible light spectrum or at a non-disturbing low-level visible light spectrum is, e.g. continuously or intermittently, provided in the room, for instance with infrared light or at a hardly visible (with human eyes) light intensity. This will not disturb the person or disrupt the person's sleep. Accordingly, in an embodiment the control unit is configured to control said illumination device to illuminate, in said first phase, said subject with invisible or low-level visible radiation to enable or support the location of the region of interest.

In a further embodiment a marker is attached to the subject's body, the subject's clothing and/or the subject's surrounding and configured to reflect or emit radiation, and said processing unit is configured to detect said marker in the radiation detected in the first phase and to locate the region of interest at a predetermined relative location with respect to said marker or at a location indicated by said marker. Said marker is functional also in the used light spectrum (e.g. at infrared wavelength used in a preferred embodiment). By use of the marker the desired region of interest can be found and/or tracked (e.g. continuously) by the processing unit based on the radiation detected by the detection device, e.g. a computer-controlled video camera, in the first phase.

When a vital sign measurement shall be taken in a second phase, a spatially confined beam of radiation (e.g. visible light in the green and/or red spectral area and—depending on the application—non-visible light in the infrared spectral area) is temporarily turned on (in addition or alternatively to the illumination used in the first phase) and directed onto the region of interest, preferably only onto this region. The region of interest can be found, as explained above, in different way, e.g. by use of a marker, which (directly or indirectly) indicates the position of the region of interest and which may also configured to actively emit light. Hereby, the marker can carry information embedded in the marker that can be retrieved in the first phase and can be used to determine the (relative) location of the region of interest with respect to the marker for guiding the illumination in the second phase. In another embodiment, the relative location of the region of interest with respect to the marker is predetermined and fixed, i.e. the control unit knows this relative location and once the position of the marker has been identified it is known where the region of interest is located.

In a preferred embodiment said illumination device comprises a first illumination unit for illuminating the subject with radiation in a first frequency range in said first phase and a second illumination unit for illuminating said region of interest of the subject with light in at least a second frequency range in said second phase, and said detection device comprises a first detection unit for receiving first radiation reflected from the subject in said first frequency range in said first phase and a second detection unit for receiving second radiation reflected from at least said region of interest of the subject in said second frequency range in said second phase. Thus, two different frequency ranges are used for the illumination in the first phase and the second phase. The detection units are adapted accordingly to be able to detect the corresponding radiation.

In an embodiment said first detection unit and said second detection unit are implemented by a common imaging unit, in particular a video camera that can detect radiation in both frequency ranges. The common imaging unit can e.g. record image data (e.g. video data), in which the position of the marker can be detected (e.g. by use of commonly known object detection algorithms) and which can be used to derive the vital sign information in the known manner. In an alternative embodiment, separate imaging units are used, e.g. an infrared camera and an RGB camera.

In an alternative embodiment said control unit is configured to control said illumination device to illuminate said region of interest with focused radiation at an increased intensity level compared to the radiation used for illumination in the first phase. Thus, in this embodiment the illumination device generally comprises a single illumination unit only for illuminating the subject and the region of interest differently in the different phases.

In another embodiment said marker comprises machine-readable information including information about the position of the region of interest, in particular a graphical pattern. The position information about the position of the region of interest can thus be encoded into the marker. Further, a graphical pattern enables the system to determine the orientation and/or location of the marker. This orientation can be used to more precisely determine the position of the region of interest.

The marker is thus used indirectly as an indicator that indicates the region of interest (ROI) to be evaluated. For example, the marker is placed on the upper arm of the patient next to the chest. In this example, the marker does not move substantially. However, the ROI is located at a known position relative to the marker. Hence, the orientation and position of the marker indicate which region of the image has to be evaluated for the determination of vital signs.

Preferably, the marker is a graphical pattern with high image contrast, for example black and white pattern. Alternatively, the graphical pattern comprises different colors that can be clearly distinguished. Favorably, the graphical pattern is optimized to be machine-readable such as a barcode, a matrix barcode or QR-code or the like. Favorably, a graphical pattern that is optimized for detectability is used.

Preferably, the system further comprises a user interface for entering information about the relative location of the ROI with respect to said marker. This enables that the user first places the marker onto the subject and then enters information into the system about the location of the ROI relative to the marker.

The illumination device, in particular the second illumination unit provided in an embodiment, can be implemented in different ways as long as it is possible to be controlled as explained and to emit radiation in an appropriate frequency range allowing the extraction of vital sign information from detected light that has been reflected from the ROI. In a preferred embodiment said illumination device (or said second illumination unit) comprises an LCD projector, an LED light source or an array of light sources.

In another embodiment the system further comprises a manipulation unit for mechanically or electronically moving and/or focusing the light beam emitted by said illumination device (in particular said second illumination unit) and/or for changing the position and/or orientation of said illumination device (in particular said second illumination unit). Thus, the illumination in the second phase can be precisely directed onto the ROI thus avoiding any disturbance of the person himself or other persons in the surrounding by visible light.

In a preferred embodiment said illumination device (in particular said second illumination unit) is configured to emit coded or modulated visible light. This provides additional robustness against other possibly interfering illumination, e.g. from other light sources, and further reduces disturbances.

Generally, several kinds of vital signs including physiological parameters in general as well as any derivative parameters (i.e. parameters derived from a physiological parameter or a vital sign) can be derived by use of the present invention. Preferably, the analysis unit is configured to determine a respiratory rate, pulse rate and/or oxygen saturation of the subject as vital sign information, in particular by use of the generally known principles of remote PPG as introduced above.

Preferably, the marker is arranged in the surrounding of the patient, e.g. on a fabric that is adapted to contact the subject or a medical item that is adapted to contact the subject. The marker can e.g. be printed onto or woven into a blanket, a bed-sheet, T-shirt, romper suit or clothing or similar items.

Alternatively, the marker is arranged on an item that is adapted to contact the subject. In general, any item can be used that has a fixed or at least relatively fixed position with respect to a ROI of the subject to be evaluated. Examples include but are not limited to any type of fixture worn by the patient, bed, cast or medical measurement equipment.

In order to increase workflow efficiency, the marker comprising a graphical pattern can be added to other items that are used in treatment of the patient already, such as a hospital gown, a blood pressure cuff or a plaster.

In an embodiment the marker is positioned on or adjacent to the face, chest, arm, hand or neck, i.e. a piece of skin, of the subject, which enables using the principles of remote PPG to derive the desired vital sign information.

In a special case the marker can be attached to the person's skin (like a band-aid) and the vital sign to be measured can be the blood oxygenation or other blood constituents. In the case of oxygen saturation it can be derived from the pulse-rate dependent periodic reflectance/color changes of the skin at or near the marker. For this measurement the skin has to be illuminated with at least two particular optical wavelengths, such as red and green light, or red and infrared light.

The orientation and/or location of the marker can further help to determine the relative location to be evaluated for vital sign measurement. For instance, the position of part of the arm or the face of the patient can be estimated from the position and/or orientation of the marker on the blood pressure cuff. A temporal variation of the skin color of the arm or face can be evaluated to determine the pulse rate of the patient.

According to a further embodiment of the present invention, the marker further comprises encoded data. Encoded data includes patient-related data such as the patient's name, hospital ward, a patient identifier. The encoded data could be a unique identifier code which allows the image processing unit to automatically pick a particular marker out of several markers. Several patients, for example each wearing a T-shirt with a distinct marker, can be monitored at the same time. Furthermore a patient can be automatically recognized when moving around the hospital, for example, while being transferred from one room to another. Still further, the encoded data can be patient specific, e.g. weight, height, etc. which can aid the identification of a patient or alternatively help in determining an appropriate region of interest for extraction of vital sign parameters. Furthermore, an error correction code can be used or encryption applied for patient privacy. The encoded data can be further used to verify markers from the original equipment manufacturer.

In a further embodiment, the machine-readable information, e.g. the graphical pattern, of the marker is invisible to the subject. For example, the marker can only be detected by an infrared camera. Alternatively, the marker comprises a combination of visible and invisible features. For example, an invisible graphical pattern is combined with a visible orientation indicator. The visible orientation indicator instructs the nurse how to place the marker, while the invisible graphical pattern can be monitored using an infrared camera even if the patient is asleep. Visible and/or infrared light sources can be applied to ensure sufficient lighting and image contrast.

In still another embodiment said processing unit is configured to detect the location of the eyes of the subject in the first phase and said control unit is configured to control said illumination device to illumination a portion of the subject's face but not the eyes in the second phase. This ensures that the eyes are never directly illuminated and that only skin is illuminated, enabling very low ambient light levels e.g. in an incubator or bedroom.

BRIEF DESCRIPTION OF THE DRAWINGS

These and other aspects of the invention will be apparent from and elucidated with reference to the embodiments described hereinafter. In the following drawings

FIGS. 9A, 9B and 9C illustrate essential steps performed by the system shown in FIG. 8 and FIGS. 10A and 10B illustrate the face illuminated by one or two illumination sources.

DETAILED DESCRIPTION OF THE INVENTION

Figure 1:
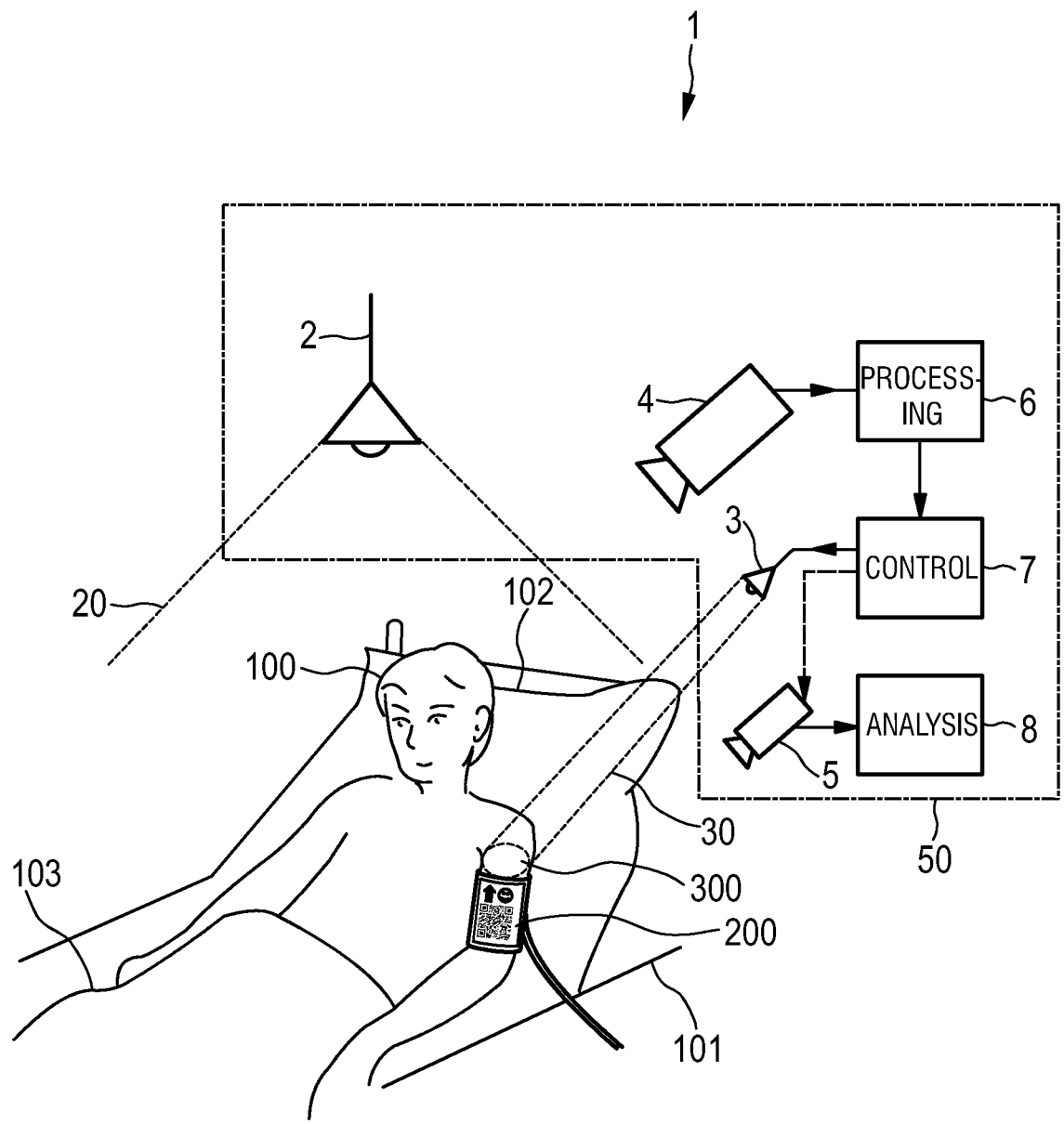
FIG. 1 shows a first embodiment of the system for determining vital sign information of a subject according to the present invention.

FIG. 1 shows a first embodiment of the system 1 for determining vital sign information of a subject according to the present invention. The subject 100, in this example a patient, lies in a bed 101, wherein the head of the subject 100 is located on a pillow 102 and the subject 100 is covered with a blanket 103. The system 1 comprises an (optional) first illumination unit 2 for illuminating the subject 100 with invisible radiation 20 in a first frequency range and a second illumination unit 3 for illuminating a region of interest (ROI) 300 of the subject 100 with visible light 30 in a second frequency range. A first detection unit 4 is provided for receiving first radiation emitted and/or reflected from the subject 100 in said first frequency range, and a second detection unit 5 is provided for receiving second radiation emitted and/or reflected from at least said ROI 300 of the subject 100 in said second frequency range.

The first illumination unit 2 and the second illumination unit 3 are for instance installed at a distance, for example at a ceiling or a wall of a room in which the bed 101 is located. Quite similarly, the first detection unit 4 and the second detection unit 5 can for instance be installed at a distance, for example at a ceiling or a wall of a room in which the bed 101 is located. In one embodiment, the first illumination unit 2 is an infrared light source and the first detection unit 4 is an infrared camera. In an embodiment the second unit 3 is a focused light source, such as a focused LED lamp, LCD projector, or an array of light sources, and the second detection unit 5 is a standard camera such as a video camera or RGB camera.

A marker 200 is attached to the subject's body or the subject's clothing. In this example the marker 200 is attached to the patient's arm in the kind of a blood pressure cuff, plaster or bandage or is even arranged on a blood pressure cuff. The marker 200 is configured to emit and/or reflect radiation in said first frequency range. A processing unit 6 is provided for detecting said marker 200 in the detected first radiation, e.g. in an image constructed from the first radiation or representing said first radiation. A control unit 7 controls said second illumination unit 3 to illuminate said ROI 300 based on the detected marker 200. Said ROI 300 is located at a predetermined relative location with respect to said marker 200 or at a location indicated by said marker 200, which may be determined in advance and/or depends on the kind of marker. Finally, an analysis unit 8 determines vital sign information of the subject 100 from the detected second radiation, or from the combination of first and second radiation.

This embodiment of the system 1 thus comprises a device 50 for determining vital sign information of a subject 100 according to the present invention and a marker 200.

The optional first illumination unit 2 can be switched on continuously since the emitted radiation (e.g. the infrared light) does not disturb the patient 100, even while sleeping. When vital sign information shall be obtained (e.g. at regular intervals) the marker 200 is detected and the ROI 300 is illuminated by the second (visible) radiation to detect radiation reflected from the ROI 300 (which is preferably a skin portion of the patient's skin). The detected radiation is then used to derive the vital sign information, e.g. the patient's pulse rate, blood pressure, oxygen saturation or other vital sign information that can be derived from the detection signals, e.g. by use of the generally remote PPG algorithm as introduced above.

Preferably, the second detection unit 5 is also controlled, as indicated by the dashed control line in FIG. 1, to detect only radiation from the ROI which is illuminated by the second illumination unit 3. In still another embodiment the second illumination unit 3 and the second detection unit can be fixedly coupled, e.g. they can be incorporated into a common housing or held by a common frame, so that they can be controlled as a common unit by a single control line and a single control signal.

Figure 2:
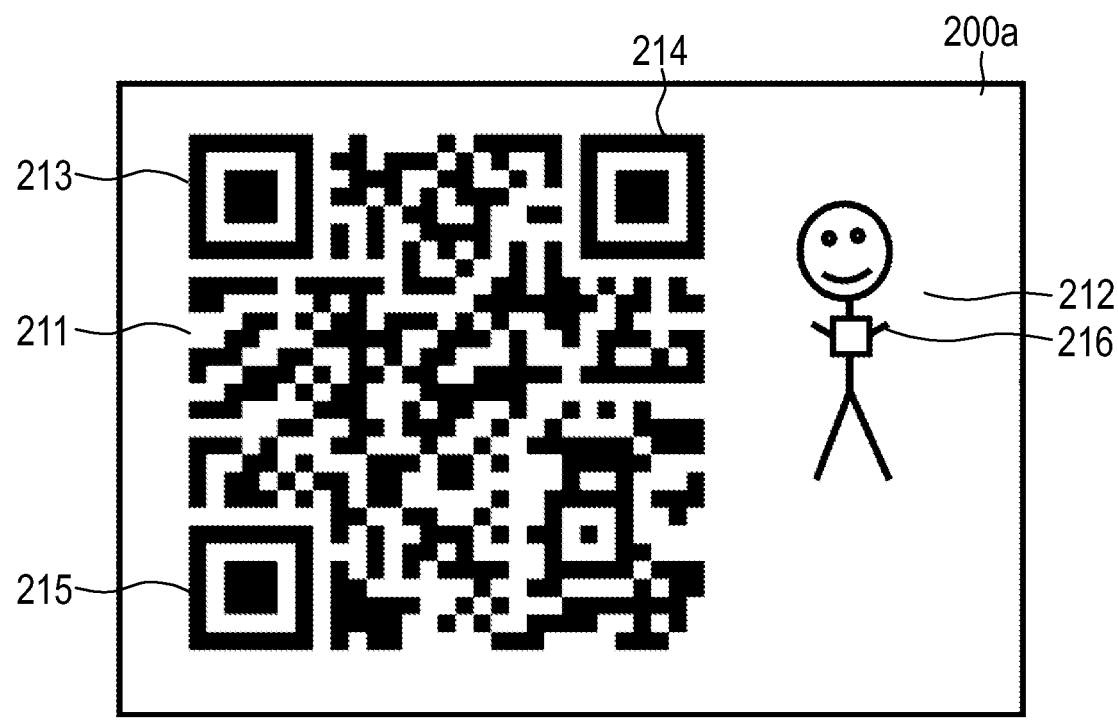
FIG. 2 shows a first example of a marker with graphical pattern.

FIG. 2 shows a first embodiment of the marker 200a comprising a graphical pattern 211 and an orientation indicator 212 for indicating the orientation of the marker. In this example, the graphical pattern 211 is a so-called QR-code. The QR-code features three structural elements 213, 214, 215 which allow for a machine-readable determination of the orientation and/or location of the pattern 211. In order to facilitate correct placement of the marker 200a on the body of the subject 100, an additional orientation indicator 212 can be implanted alongside with the graphical pattern 211. In this example, the orientation indicator is a pictogram of a person that shows the position 216 where to place the marker 200a. Thus, the relative position of the ROI 300 with respect to the marker 200a is predetermined, e.g. the ROI is located just above the marker 200a on the upper side of the arm. Thus, the control unit 7 controls the second illumination unit 3 to illuminate this area whose position is determined after the location and orientation of the marker has been precisely determined by the processing unit 6.

The marker 200a can be made out of paper, cloth, rubber, or a similar material. As an example, one may picture a computer mouse pad, which has a rubbery bottom surface which keeps it from sliding. The graphical pattern 211 will then be printed on the top surface of the "mouse pad".

The graphical pattern 211 can be generated through a computer program and can be printed on the material. In case of the QR-code, patient specific data can be encoded along with error protection or encryption of the data. Alternatively, other types of machine-readable graphical patterns can be employed.

In another implementation the marker on the subject can be a marking directly applied to the subject or his clothing, e.g. a marking drawn with a pen (such as a simple sign (e.g. a circle or arrow) applied by a nurse. Further, in an embodiment the marker can be configured to actively emit radiation (e.g. visible light) to enable the detection of the location of the marker.

Figure 3:
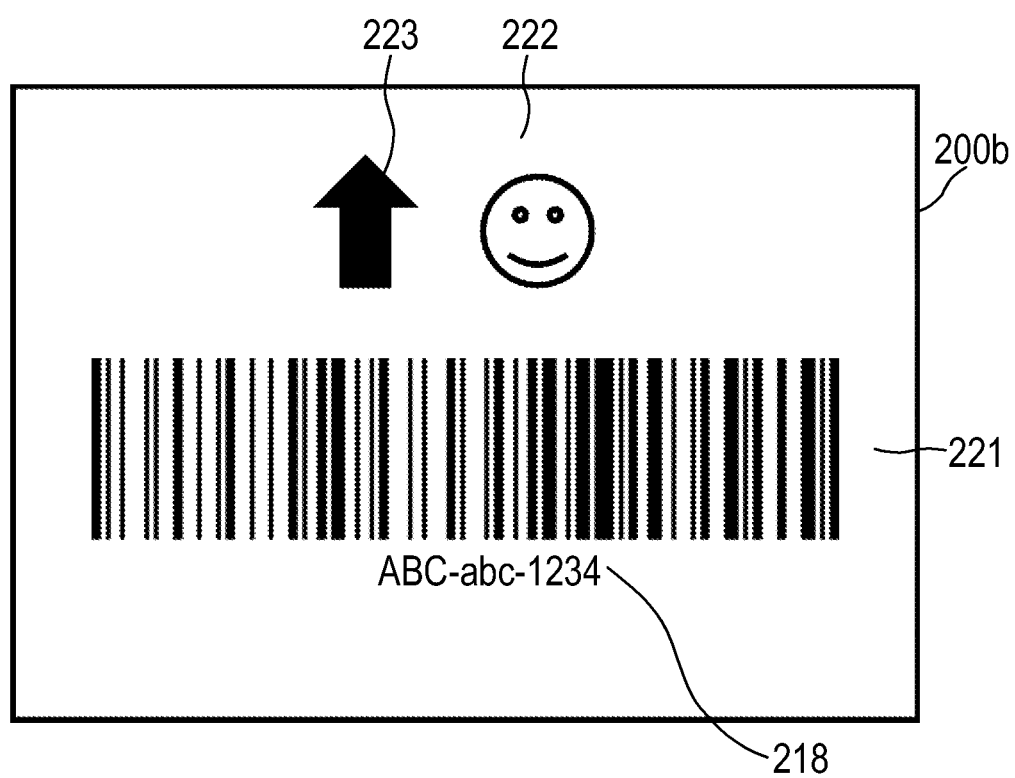
FIG. 3 shows a second example of a marker with graphical pattern.

FIG. 3 shows an alternative embodiment of the marker 200b with a graphical pattern in form of a barcode 221. Furthermore, the marker 200b comprises an orientation indicator with an arrow 223 and a pictogram 222 of a face that has to be aligned so as to point at the face of the subject 100. Data is encoded in the barcode 221 and, in an embodiment, printed as text 218. Thus, in this embodiment the arrow 223 is detected by the processing unit and indicates the position of the ROI (e.g. here a piece of the patient's cheek) which is located just above next to the tip of the arrow 223. The control unit 7 thus controls the second illumination unit 3 to illuminate this area.

As shown in FIG. 1 the marker 200 can be directly attached to the body of the subject 100, e.g. by placing it on or close to a piece of skin such as the arm, hand, chest, neck etc. of the subject 100. In other embodiments the marker 200 can be attached or integrated into a piece of cloth, such as clothing of the subject, the blanket or something else arranged at the patient, e.g. a medical item.

In a preferred alternative embodiment the marker comprises machine-readable information including information about the position (and eventually the size) of the ROI 300 with respect to the marker 200. Hence, this information is read by the processing unit 6 and forwarded to the control unit 7 to control the second illumination unit 3 appropriately in accordance with the information stored on the marker.

Figure 4:
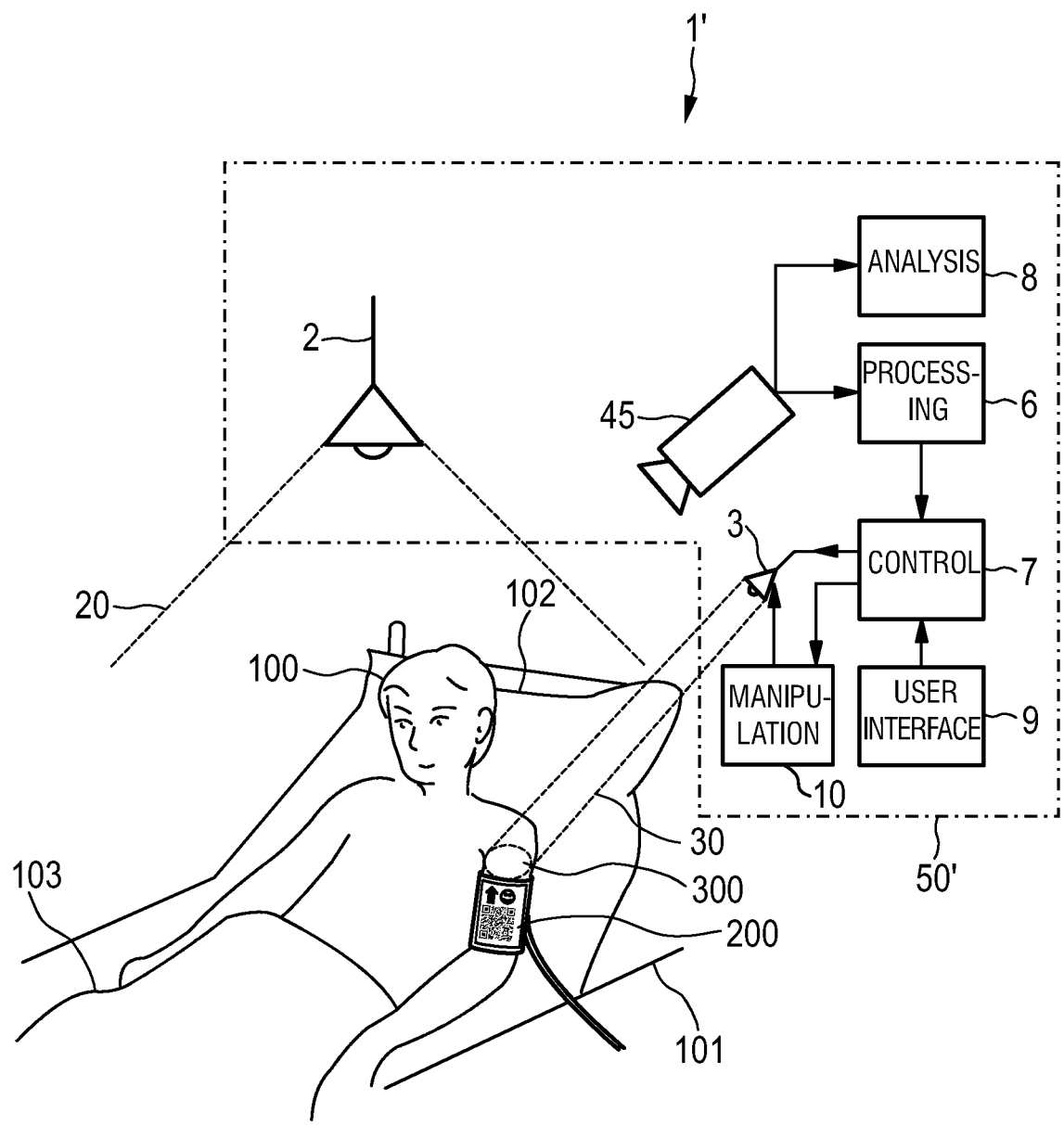
FIG. 4 shows a second embodiment of the system of the present invention.

FIG. 4 shows a second embodiment of the system 1' of the present invention comprising a second embodiment of a device 50' for determining vital sign information of a subject 100 according to the present invention. In this embodiment the first detection unit 4 and the second detection unit 5 are implemented by a common imaging unit 45, in particular a video camera. Generally, the first and second illumination units 2 and 3 could also be implemented by a common illumination unit (not shown) as long as it is possible to switch between the different illumination modes realized by the two illumination modes.

Further, a user interface 9 is provided for entering information about the relative location of the ROI 300 with respect to the marker 200 into the control unit 7. Thus, a user can program the control unit 7 to position the second illumination unit 3 onto a programmed area with respect to the position of the marker 200, e.g. at a certain amount of centimeters in a certain direction. Thus, the position of the ROI 300 can be individually determined once the marker has been attached to the subject 100.

Still further, a manipulation unit 10 for mechanically or electronically moving and/or focusing the light beam emitted by said second illumination unit 3 and/or for changing the position and/or orientation of said second illumination unit 3 is provided. This manipulation unit 10 may include an actuator or motor that can manipulate the second illumination unit 3. Alternatively and/or in addition manipulation means may be implemented within the second illumination unit 3, such as focusing means for optically changing the focus and/or direction of the radiation beam 30. A manipulation unit 10' (or separate manipulation means) may further be used to manipulate the detection unit 45 (or the second detection unit 5) in the same manner as illustrated in FIG. 6.

Preferably, in still another embodiment the second illumination unit 3 is configured to emit coded or modulated visible light, thus preferably avoiding any interference or disturbance with other light sources. In addition, additional information, e.g. related to the patient, can be encoded into the visible light.

Figure 5:
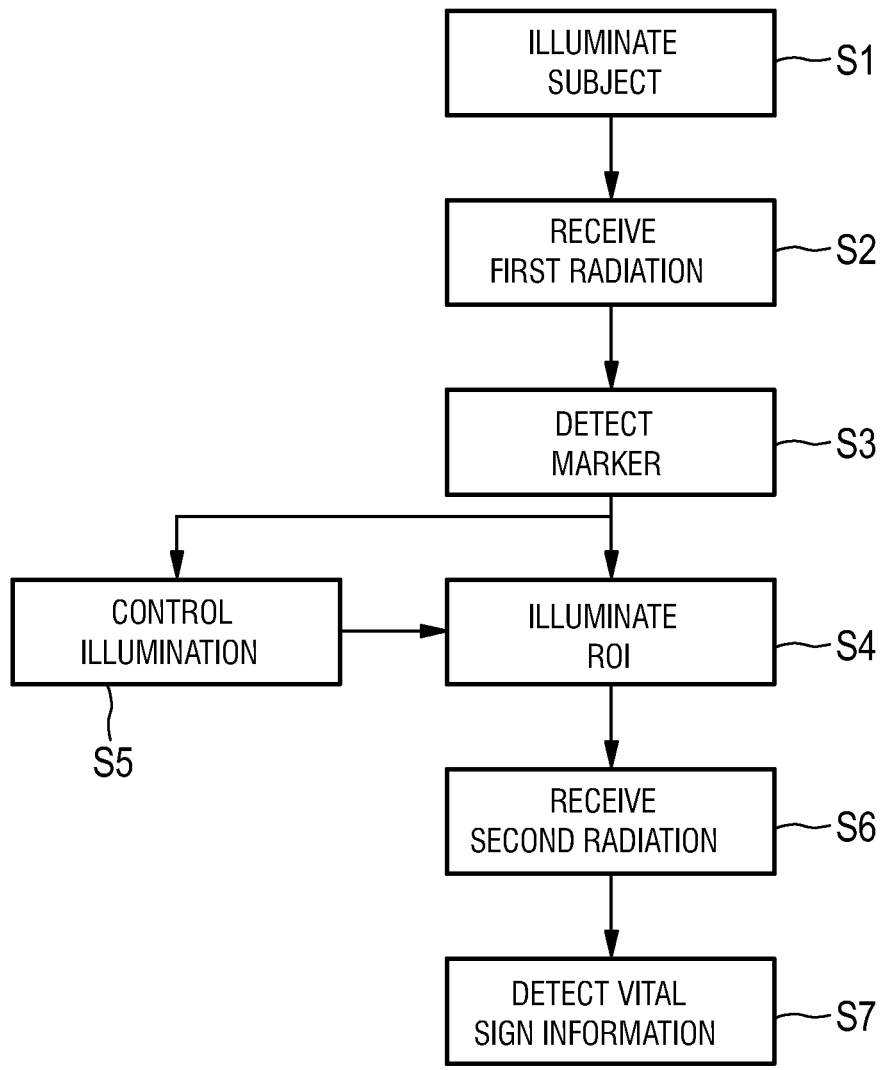
FIG. 5 shows the process flow of a first embodiment of a method for determining vital sign information according to the present invention.

FIG. 5 shows a process flow for determining vital sign information of a subject according to an embodiment. The subject is illuminated (step S1) with invisible radiation in a first frequency range, and first radiation emitted and/or reflected from the subject in said first frequency range is received (S2). In the detected first radiation a marker, which is attached to the subject's body or the subject's clothing and configured to emit and/or reflect radiation in said first frequency range, is detected (S3). Further, a region of interest of the subject is illuminated (S4) with visible light in a second frequency range. This illumination is controlled (S5) based on the detected marker, said region of interest being located at a predetermined relative location with respect to said marker or at a location indicated by said marker. Second radiation emitted and/or reflected from at least said region of interest of the subject in said second frequency range is detected (S6) from which vital sign information of the subject is detected (S7).

Figure 6:
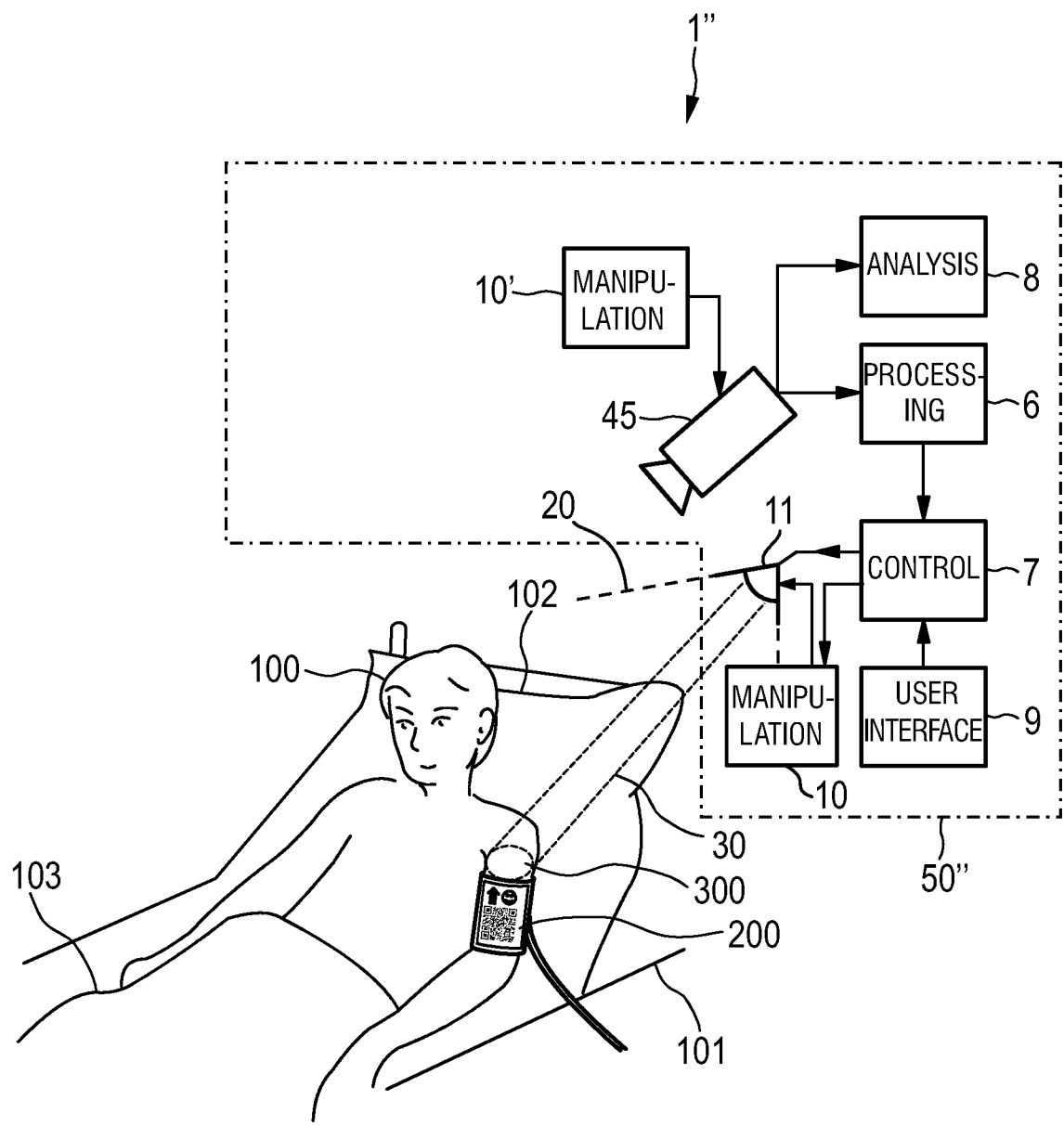
FIG. 6 shows a third embodiment of the system of the present invention.

FIG. 6 shows a third embodiment of the system 1" of the present invention comprising a third embodiment of a device 50" for determining vital sign information of a subject 100 according to the present invention. In this embodiment the system comprises a single illumination device 11 for illuminating the subject 100 with radiation and a single detection device 45 for receiving radiation reflected from the subject 100. The optional marker 200 is attached to the subject's body or the subject's clothing and configured to reflect radiation. The control unit 7 is configured to control said illumination device 11 to illuminate, in a first phase, said subject 100 with invisible or low-level visible radiation 20 allowing detection of the region of interest (optionally using said marker) and to illuminate, in a second phase, the located region of interest 300 with radiation 30 allowing determination of vital sign information.

If a marker 200 is used, as shown in FIG. 6, locating the region of interest 300 is based on the detected marker 200, said region of interest 300 being located at a predetermined relative location with respect to said marker or at a location indicated by said marker. The processing unit 6 detects said marker in the radiation detected in the first phase, and the analysis unit 8 determines vital sign information of the subject from the radiation reflected from said region of interest 300 and detected in said second phase.

The control unit 7 particularly controls said illumination device 11 to locally illuminate said region of interest 300 with focused radiation at an increased intensity level compared to the radiation used for illumination in the first phase. Thus, the illumination device 11 can preferably be controlled in respect of its intensity and its illumination angle (e.g. by use of lenses, filters, diaphragms, array of light emitters that are selectively controllable or the like). In another embodiment the illumination device 11 is composed of different illumination elements, one that provides a wide angle low intensity illumination during the first phase and a second illumination element with a more focused, higher intensity illumination for the region of interest in the second phase. Further, in an embodiment the illumination device 11 can be controlled in its frequency range used for the illumination. In a preferred embodiment the illumination used in the first phase is such that it is not disturbing the subject and can be used at intervals or even continuously. The illumination in the second phase can then be switched on additionally or alternatively to the illumination used in the first phase.

In still another embodiment no markers are used. In this embodiment the processing unit 6 is configured to locate the region of interest in a first phase without using the help of marker. For instance, known image processing techniques can be used which can identify anatomic properties of the subject 100 and to locate the region of interest based on identified anatomic properties. In the first phase an additional illumination with radiation (e.g. infrared light or visible light at a low level) can be used, or only the ambient light can be used to perform the location of the region of interest 300.

Further, in this embodiment the control unit 7 is configured to control said illumination device 11 to locally illuminate, in the second phase, the located region of interest with radiation allowing determination of vital sign information. Thus, the location information about the located region of interest is evaluated to provide a targeted illumination of the region of interest 300.

Figure 7:
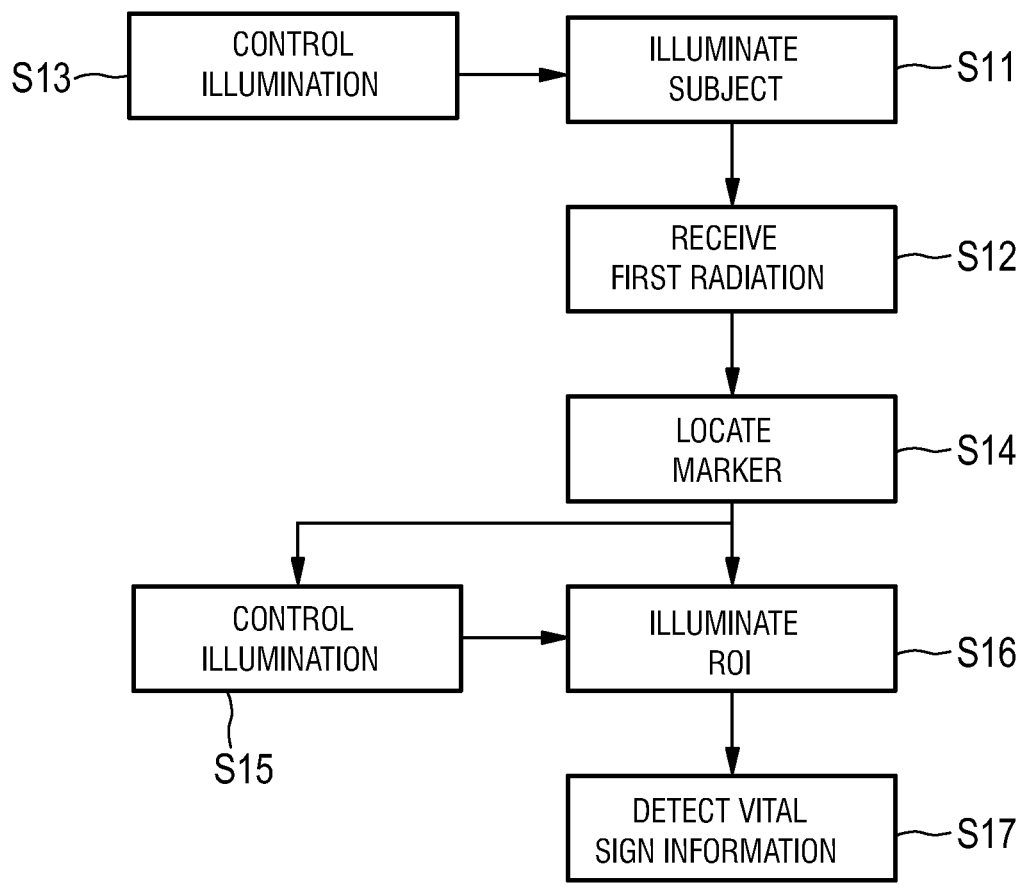
FIG. 7 shows the process flow of a second embodiment of a method for determining vital sign information according to the present invention.

FIG. 7 shows a process flow for determining vital sign information of a subject according to another embodiment. The subject is illuminated (step S11) with radiation, and radiation reflected from the subject is received (S12). Said illumination is controlled (S13) to illuminate, in a first phase, said subject with invisible or low-level visible radiation allowing location of the region of interest, e.g. by detection of said marker. The location of the region of interest, e.g. the marker, is determined (S14) in the radiation detected in the first phase. Based thereon the illumination is controlled (S15) to locally illuminate, in a second phase (S16), the located region of interest with radiation allowing determination of vital sign information.

When the optional marker is used, the region of interest is determined (i.e. located) by detecting the marker (S14) in the first phase and based on the detected marker, said region of interest being located at a predetermined relative location with respect to said marker or at a location indicated by said marker, said marker being attached to the subject's body or the subject's clothing and configured to reflect radiation. Finally, vital sign information of the subject is determined (S17) from the radiation reflected from said region of interest and detected in said second phase.

In this context it shall be noted that particularly visible light may not only be disturbing to a person, but also can be dangerous if it exceeds a certain level in the eyes (of a person or animal), even (or especially) when the person doesn't recognize it as visible light. Therefore the present invention additionally represents an important safety feature in selected applications (e.g. when used in the context of neonatal monitoring) if the light level that is needed for an accurate measurement exceeds the safety limits for the eyes.

The present invention may advantageously be applied for monitoring of SpO2 (oxygen saturation of arterial blood). SpO2 measurement can be performed using a camera, much similar to how this is realized in a contact sensor, i.e. by measuring the light reflected back from the skin of a subject. This light is modulated by the pulsatile arteries and the modulation amplitude contains the information of the blood saturation levels. In practice, SpO2 is computed by measuring this PPG amplitude (caused by pulsatile blood in arteries) at two distinct wavelengths. The ratio between the PPG amplitudes (DC normalized) of the two wavelengths gives the following equation for the computation of SpO2:

$$SpO_2 = C_1 - C_2 \frac{R}{IR}$$

where $$R = \frac{AC_{RED}}{DC_{RED}} \text{ and } IR = \frac{AC_{IR}}{DC_{IR}}.$$

This measurement technique requires that the skin is illuminated at the red and infrared (IR) wavelengths. Ambient illumination can, in principle, be used but the low illumination levels in the desired wavelengths (IR in particular) and the poor temporal stability have the consequence that dedicated illumination is preferred.

With dedicated illumination the temporal characteristic of the intensity (either stability or modulation) can be controlled and it can be ensured that it has sufficient IR. But with the sensitivity of current cameras substantial levels of (visible) red light are required. This is often undesired because vital signs need often be measured in near dark settings (e.g. NICU, or bedroom).

The usually used illumination setup comprises one or more incandescent lamps. This usually used setup does not discriminate between the skin (from which the vital signs are measured) and other structures which should not be illuminated, such as eyes, whole upper body and non-skin structures from which no SpO2 can be measured. However, illumination of clothing and blankets does not contribute to the measurement of SpO2. In fact, it can disturb the measurement when these objects move. Moreover, light reflected off these objects adds to the overall ambient light level, causing possible discomfort to anybody in that room.

According to the present invention a smarter illumination is provided which can make this distinction and only illuminates the face but not the eyes. This allows the use of illumination levels sufficiently high for SpO2 measurement without causing discomfort to the subject or others, either by direct illumination to the eye or by a high overall ambient illumination level. According to a preferred embodiment the location of the face and eyes is identified, and subsequently only the face area is illuminated (avoiding illumination of blankets and other objects), but without illuminating the eyes.

Figure 8:
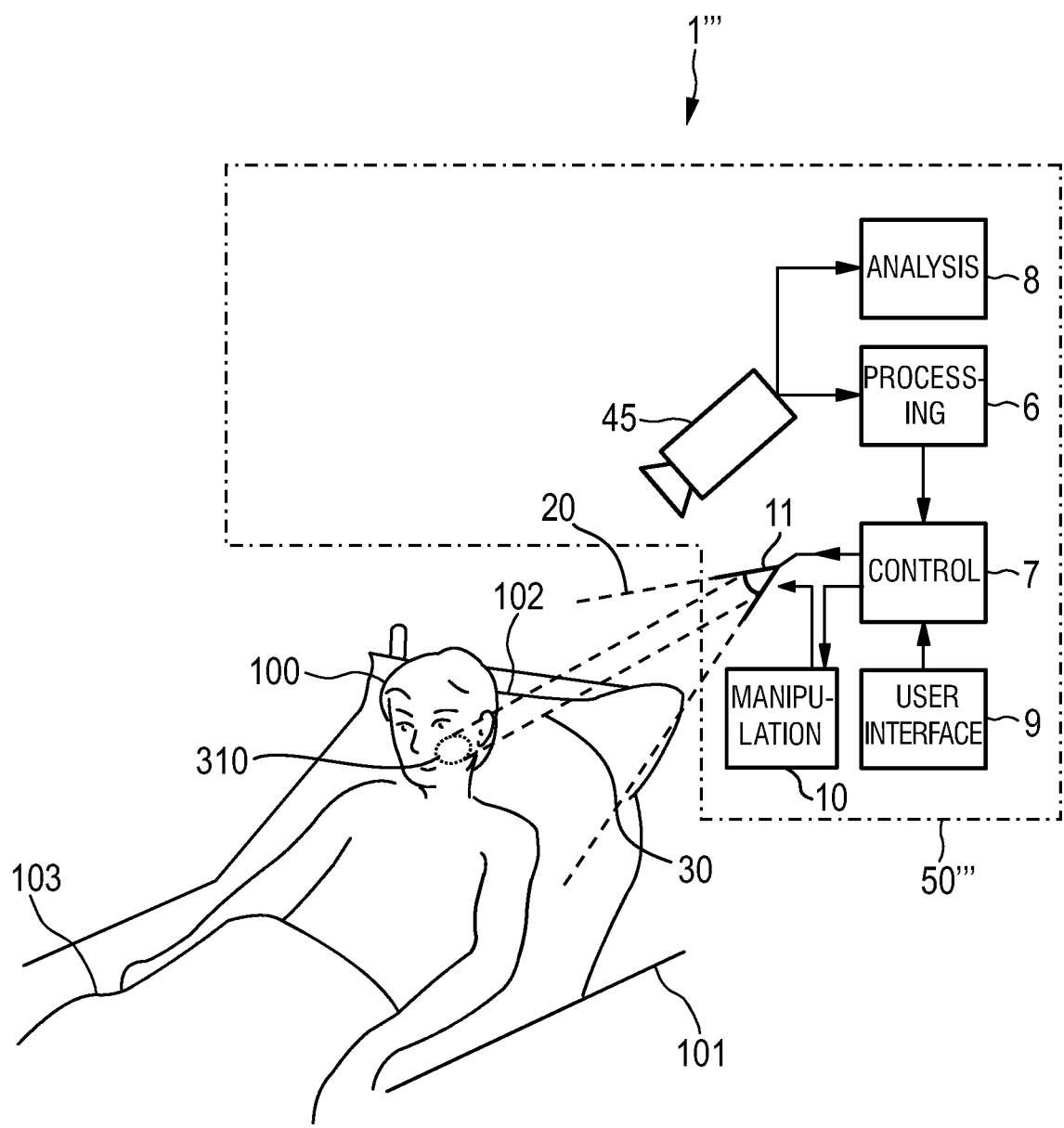
FIG. 8 shows a fourth embodiment of the system of the present invention.

FIG. 8 shows a fourth embodiment of the system 1''' comprising a fourth embodiment of a device 50''' for determining vital sign information of a subject 100 according to the present invention. It comprises one (or more) camera(s) and one (or more) projector(s) (=light sources). The camera 45 captures an image of the subject (as shown in FIG. 9A) with infrared light IRdet 20 provided by the illumination device 11. From this image the face and the location of eyes is identified (as shown in FIG. 9B) by the processing unit 6. This can be done with standard face detection algorithms or with known eye tracking algorithms based on an initial region of interest selection, which may be done manually (e.g. via the optionally provided user interface 9) or automatically. This information is used for controlling the illumination device 11 to only illuminate the face, e.g. an area 310 of the cheeks, 20 excluding the eyes (as shown in FIG. 9C) with light 30 required for obtaining the desired vital signs, e.g. with visible red light for obtaining SPO2 information.

The IRdet illumination (for detection of the face and eyes) is separated from the infrared light IRmeas used for measurement either by time sequencing or by wavelength band separation. The intensity of IRdet is preferably such that it does not cause eye (or any other) damage.

Said system 1''' may also have multiple illumination sources like the systems 1 and 1' explained above. One disadvantage of having just one illumination source is that the illumination for SpO2 measurement is from a point source. The irradiance on the skin then depends strongly on the orientation of the skin with respect to the illumination source. With multiple illumination sources, illuminating skin from a range of angles, this effect is drastically reduced as shown in FIG. 10. If there is no motion (relative orientation of skin to illumination source remains constant) there is not so much a problem but even the slightest motion (relative orientation of skin to illumination source changes)

the sensitive PPG signals can be easily disturbed. This disturbance can be drastically reduced with illumination from different angles. A face illuminated by a point source (to the left of the face) as shown in FIG. 10A gives rise to relatively strong gradients of illumination due to strong dependence of skin orientation to illumination source. Multiple illumination sources all around the face drastically reduce the strong gradients of illumination as shown in FIG. 10B.

It shall be noted that the fourth embodiment illustrated in FIGS. 8 to 10 is not limited to the determination of SPO2, but can also be used for determining other vital signs.

The present invention thus provides that accurate and reliable vital sign measurements can be made in darkness or low-light conditions with causing any trouble to the subject himself, in particular a person or animal, and other persons nearby.

The measured vital sign information can be automatically provided to a doctor or to a hospital computer system. The proposed system for determining a vital sign of a subject is intended for use in a hospital, at a clinic, at a doctor or for monitoring patients at home. The system can, for instance, be installed in a hospital room but also in an incubator, e.g., in a neonatal ICU (NICU), e.g. for measurement of SpO2 for NICU. But other (not necessarily medical) applications of the invention are generally possible.

The contactless monitoring is assumed to be highly relevant for premature babies with very sensitive skin in NICUs, and for patients with damaged (e.g. burns) skin, but may also be more convenient than contact sensors as used in the general ward. Another application could be in home healthcare, where, at times, the subject needs to be monitored in a dark environment. The present invention would ensure the subject is minimally disturbed and the illumination levels are adequate for a proper measurement. Another application is the automotive measurement of vital signs. Ensuring the light does not fall on a subject's eyes will prevent any risks during driving. other (not necessarily medical) applications of the invention are generally possible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for determining vital sign information of a subject comprising:
   an illumination device configured to illuminate the subject with radiation of a first intensity level during a first phase,
   a detection device configured to receive radiation reflected from the subject during the first phase,
   a processing unit configured to locate a region of interest from the reflected radiation in the first phase,
   a control unit configured to control said illumination device to locally illuminate, in a second phase, only the located region of interest with radiation of a second intensity level greater than the first intensity level such that in the second phase, reflected radiation includes vital sign information, and
   an analysis unit configured to determine vital sign information of the subject from the radiation reflected from said region of interest detected in said second phase.

2. The system according to claim 1, wherein said control unit is configured to control said illumination device to illuminate, in said first phase, said subject with invisible or low-level visible radiation to enable or support locating the region of interest.

3. The system according to claim 2, wherein:
   said illumination device comprises a first illumination unit configured to illuminate the subject with radiation in a first frequency range in said first phase and a second illumination unit configured to illuminate said region of interest of the subject with light in at least a second frequency range in said second phase;
   said detection device comprises a first detection unit configured to receive first radiation reflected from the subject in said first frequency range in said first phase and a second detection unit configured to receive second radiation reflected from at least said region of interest of the subject in said second frequency range in said second phase; and
   the first frequency range is different than the second frequency range.

4. The system according to claim 3, wherein said first detection unit and said second detection unit are implemented by a common imaging unit, wherein the common imaging unit is a video camera configured to detect radiation in both the first frequency range and the second frequency range.

5. The system according to claim 3, wherein said first illumination unit is configured to illuminate the subject with infrared radiation.

6. The system according to claim 1. further comprising a marker attached to the subject's body, the subject's clothing and/or the subject's surrounding and configured to reflect or emit radiation;
   wherein said processing unit is configured to detect said marker in the radiation detected in the first phase and to locate the region of interest at a predetermined relative location with respect to said marker or at a location indicated by said marker.

7. The system according to claim 6, wherein:
   said marker comprises machine-readable information including information about the position of the region of interest; and said marker comprises a graphical pattern.

8. The system according to claim 6, further comprising a user interface configured for entering an information about the relative location of the region of interest with respect to said marker.

9. The system according to claim I, wherein said illumination device comprises an LCD projector, an LED light source or an array of light sources.

10. The system according to claim I, further comprising a manipulation unit for mechanically or electronically moving and/or focusing the light beam emitted by said illumination device and/or for changing the position and/or orientation of said illumination device.

11. The system according to claim 1, wherein said illumination device is configured to emit coded or modulated visible light in said second phase.

12. The system according to claim 6, wherein the marker is arranged on a fabric that is adapted to contact the subject or a medical item that is adapted to contact the subject.

13. The system according to claim 6, wherein the marker is positioned on or adjacent to the face, chest, arm, hand or neck of the subject.

14. The system according to claim 1, wherein said processing unit is configured to detect the location of the eyes of the subject in the first phase and said control unit is configured to control said illumination device to illumination a portion of the subject's face but not the eyes in the second phase.

15. A method for determining vital sign information of a subject comprising:
   illuminating the subject with radiation,
   receiving radiation reflected from the subject,
   automatically locating a region of interest in a first phase, said region of interest being a skin portion of the subject's skin, wherein the radiation that illuminates the subject during the first phase is of a first intensity level,
   controlling said illumination to locally illuminate, in a second phase, the located region of interest with radiation of a second intensity level greater than the first intensity level thereby allowing determination of vital sign information, and
   determining current vital sign information of the subject from the radiation reflected from said region of interest detected in said second phase by use of remote photoplethysmography.

16. A computer readable non-transitory medium having instructions stored thereon which, when carried out on a computer, cause the computer to perform the method of claim 15.

17. A system for determining vital sign information of a subject comprising:
   a light configured to illuminate the subject with radiation,
   a detector configured to receive light reflected from the subject,
   one or more computer processors configured to:
      locate a region of interest from detected, reflected light in a first phase,
      control said light to locally illuminate only the located region of interest, in a second phase, with light of a different frequency than in the first phase, and
      determine vital sign information of the subject from the light reflected from said region of interest detected in said second phase.

18. The system of claim 17, wherein the one or more processors are further configured to locate the region of interest during the first phase based on a marker comprising machine-readable information including information about a position and a size of the region of interest.

19. The system of claim 17 wherein:
the light that illuminates the subject during the first phase is of a first intensity level, and
the light that illuminates the located region of interest during the second phase is of a second intensity level greater than the first intensity level.

20. The system of claim 17 wherein:
the light that illuminates the subject during the second phase is more focused than the light that illuminates the subject during the first phase.

* * * * *